(12) United States Patent
Ekström

(10) Patent No.: US 6,523,723 B1
(45) Date of Patent: Feb. 25, 2003

(54) DOSING FEEDER FOR LIQUIDS

(76) Inventor: Sten Ekström, Solbacksvägen 13, S-642 32 Flen (SE)

( * ) Notice: Subject to any disclaimer, the term of this patent is extended or adjusted under 35 U.S.C. 154(b) by 0 days.

(21) Appl. No.: 09/787,379

(22) PCT Filed: Sep. 2, 1999

(86) PCT No.: PCT/SE99/01509
§ 371 (c)(1),
(2), (4) Date: Mar. 28, 2001

(87) PCT Pub. No.: WO00/21460
PCT Pub. Date: Apr. 20, 2000

(30) Foreign Application Priority Data

Sep. 28, 1998 (SE) .............................................. 9803269

(51) Int. Cl.[7] ........................ A61C 19/00; B65D 47/20; B65D 83/00
(52) U.S. Cl. ........................ 222/165; 222/71; 222/166; 222/170; 222/444; 222/454; 222/584; 141/319
(58) Field of Search ................................. 222/164–167, 222/169–172, 71, 444, 454–456, 584; 141/319–322

(56) References Cited

U.S. PATENT DOCUMENTS 1,753,278 A * 8/1930 Westberg et al. ........... 222/165
2,046,068 A * 6/1936 Gray ........................... 222/165

* cited by examiner

*Primary Examiner*—J. Casimer Jacyna
(74) *Attorney, Agent, or Firm*—Dykema Gossett PLLC

(57) ABSTRACT

Dosing feeder for a liquid that is in a container (6), comprising a dosing arm (2) that shows at least one dosing cup (2.1) that is open at the top. The dosing arm (2) is arranged in a dosing head (3) that in its turn shows a first duct (4.1) being in connection with the container (6). The dosing head (3) is movable or turnable in relation to the dosing arm (2) so that the dosing cup (2.1) alternately may be brought in connection with the first duct (4.1) for feed of liquid or may release the dosing cup (2.1) so that it gets accessible for the liquid. The dosing arm (2) may be cylinder-shaped, the dosing head (3) being turnable around the dosing arm (2). On filling with liquid into the dosing cup (2.1) the container (6) is above the dosing arm (2), the first duct (4.1) being connected with the dosing cup (2.1.). In position of rest the container (6) is under the dosing arm (2), the second duct (3.2) being connected with the dosing cup (2.1).

7 Claims, 2 Drawing Sheets

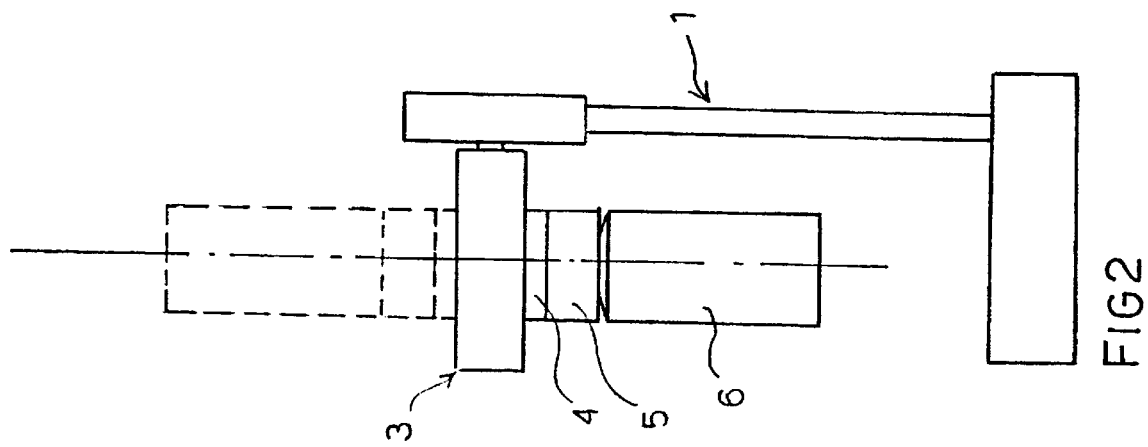
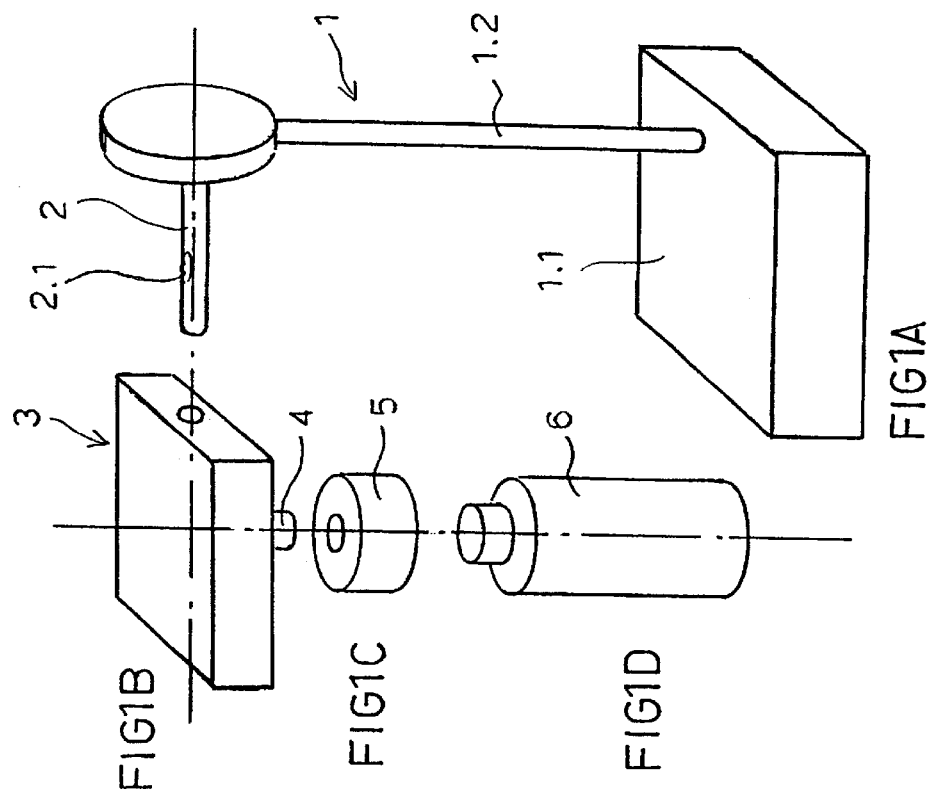

DOSING FEEDER FOR LIQUIDS

BACKGROUND OF THE INVENTION

1. Field of the Invention

The present invention relates to a dosing feeder for preferably small amounts of liquid which, when in contact with skin or eyes, may cause injuries, e.g., in medical treatment and dental care, particularly bonding liquid for mending or filling of cavities with UV-light hardening plastic materials.

2. The Prior Art

In dosing preferably small amounts of liquid which, when in contact with skin or eyes, may cause injuries, e.g., in medical treatment and dental care, protective equipment is required that often is difficult to use, e.g., plastic gloves and safety goggles, in order to prevent injuries in the event the aggressive liquid splashes, above all in connection with the dosing itself, but also to prevent skin contact with dosing equipment such as pipettes and dropping bottles that are wetted on the outside by the liquid concerned. A typical liquid of that sort is the liquid used in dental care as bonding liquid when mending or filling cavities with UV-light hardening plastic materials. It is very difficult for the treating dentist to protect himself from skin contact with the bonding liquid as a number of treatment steps are going on simultaneously and cannot be interrupted, e.g., in order to put on or to change protective gloves. At the same time, it is very expensive to have personnel with protective equipment available to handle the dosing and serve the attending dentist.

DESCRIPTION OF THE INVENTION

The object of the present invention is to provide a dosing feeder for injurious liquids that avoids the above-mentioned disadvantages with special protective equipment.

The object is achieved with a dosing feeder that includes a dosing arm that includes at least one dosing cup which is open at the top and arranged in a corresponding opening in a dosing head that in its turn includes a first duct in connection with the container. The dosing head is movable or turnable in relation to the dosing arm so that the dosing cup alternately may be brought in connection with the first duct for the feed of liquid or may release the dosing cup so that it becomes accessible for the liquid. The dosing head may alternately be constructed to include two or more dosing cups of different sizes and on filling, the desired cup is chosen by a linear movement of the dosing head and that cup is made accessible by either a further linear movement or a rotation of the dosing head.

In a practical embodiment a linearly movable dosing head may then have the liquid container fixed on the upper side, but also a liquid container that is stationary fixed, e.g. on a stand and that is connected with the first duct via a flexible hose.

Preferably also a second duct is arranged in the dosing head and accessible from above and admits accessibility to the dosing cup when the first duct to the liquid container is brought out of connection with the same.

In a preferred embodiment the dosing arm is cylinder-shaped, the dosing head being turnable around the dosing arm. The first duct is on one side of the dosing arm and the second duct is on the other side of the dosing arm, both ducts showing mainly the same direction of extension. When filling liquid into the dosing cup, the container is above the dosing arm and the first duct is connected with the dosing cup. The container is in position of rest under the dosing arm, the second duct being connected with the dosing cup. Also in this embodiment the dosing arm may show two or more dosing cups, where the desired dosing cup is chosen by a linear movement of the dosing head.

Further features and characteristics concerning the present invention will become evident from the description of the attached drawings.

DESCRIPTION TO THE DRAWINGS

FIGS. 1A–1D show a disassembled view of a preferred embodiment of a dosing feeder according to the invention with a container containing bonding liquid.

FIG. 2 shows the dosing feeder according to FIGS. 1A–1D in assembled state.

DETAILED DESCRIPTION OF THE PREFERRED EMBODIMENT

Figure 3:
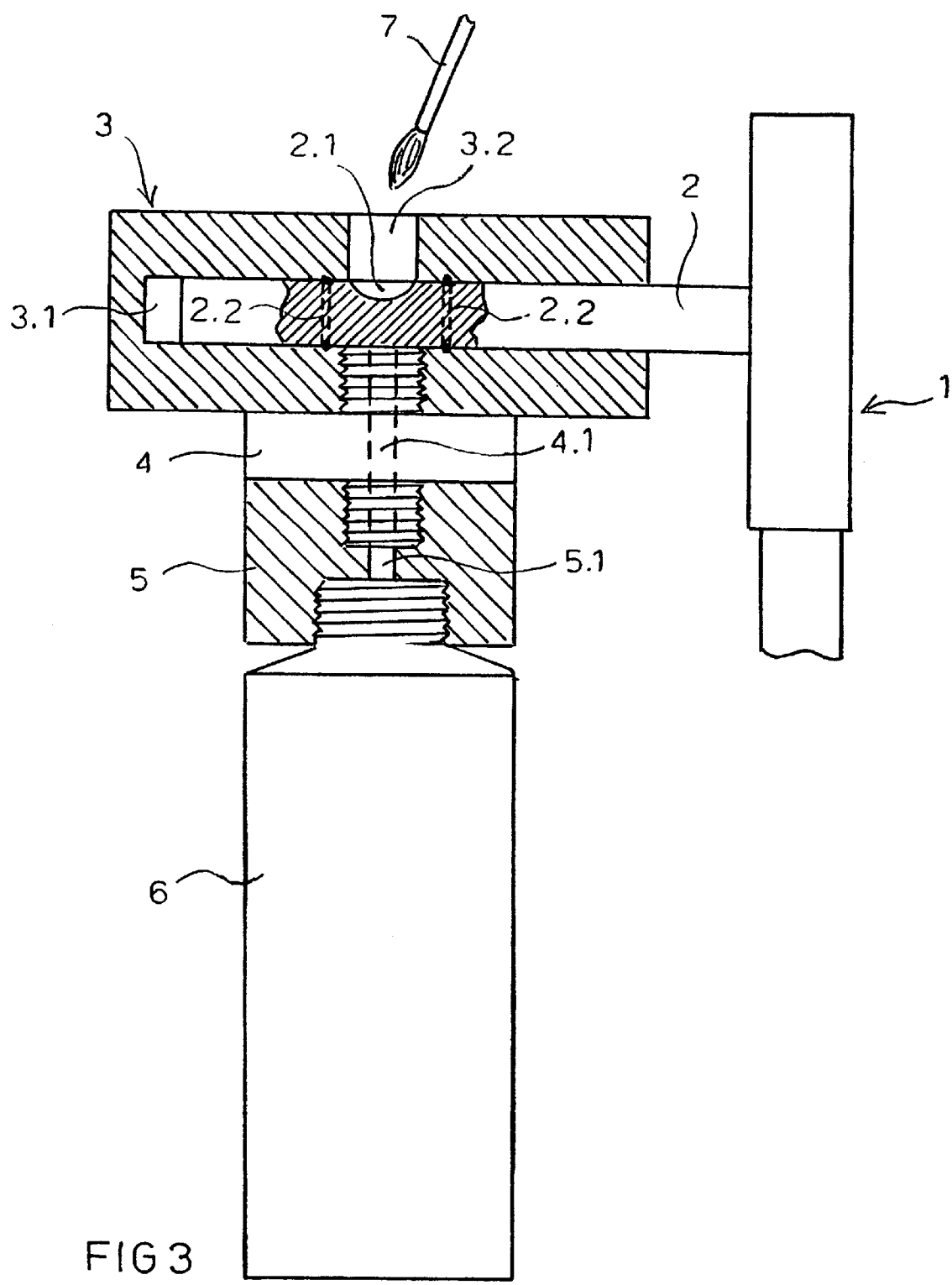
FIG. 3 shows a detail of the dosing feeder according to FIG. 2, partly in a longitudinal section, through the direction of its longitudinal axis.

The dosing feeder shown in the figures comprises a stand 1 having a base plate 1.1 and, vertically projecting from it, a rod 1.2 having a dosing arm 2 fixedly arranged at its upper end. The dosing arm 2 is cylinder-shaped and includes an open dosing cup 2.1 in the form of a cut-in portion in its upper surface. The dosing arm 2 carries in its turn a dosing head 3, in which the dosing arm 2 is introduced in a corresponding cylinder-shaped hole 3.1. The dosing head 3 is turnable around the dosing arm 2 and includes on one of its sides a fitting 4 for an adapter 5 to which a container 6, containing bonding liquid, is intended to be connected. The container 6 connected to the adapter 5 is shown in FIG. 3. The adapter 5 includes partly a thread cutting that corresponds with the screw threading of the fitting 4 of the dosing head and partly a thread cutting corresponding the screw threading of the container and a third duct 5.1 through which bonding liquid can flow in filling the dosing cup 2.1. The fitting 4 includes a first through duct 4.1 for liquid that extends to the dosing arm 2.

The dosing head 3 includes further a second duct 3.2 with the same direction of axis as the first duct 4.1 on the other side of the dosing arm 2 and that has a somewhat larger diameter corresponding the diameter of the dosing cup 2.1. A packing 2.2 in the form of an O-ring, as it is called, is arranged in different notches of the dosing arm 2 on each side of the dosing cup 2.1 and prevents bonding liquid from flowing out from the slot between the dosing arm 2 and the opening 3.1 in the dosing head 3.

The dosing feeder shown in the figures is used in the following way. When the dosing head 3 is turned so that the container 6 with the bonding liquid is vertically above the dosing arm 2, the first duct 4.1 is brought into the fitting 4 and the third duct 5.1 in the adapter 5 into connection with the dosing cup 2.1 that then is filled with bonding liquid. This position is shown with broken lines in FIG. 2. When the dosing head 3 is turned back into its initial position with the container 6 vertically under the dosing arm 2, the bonding liquid that is left in the first duct 4.1 and in the third duct 5.1 flows back into the container 6. A dose of bonding liquid now is left in the dosing cup 2.1 and is accessible with, e.g., a brush 7 that can be introduced through the second duct 3.2 and be brought to pick up bonding liquid, which then can be applied to the tooth to be mended.

Dosing cups 2.1 of different sizes may be arranged along the dosing arm 2, not shown in the figures, the dosing head 3 may being moved axially along the dosing arm 2 to a desired size of the dosing cup 2.1.

It also lies within the scope of the invention to let the dosing head 3 be only linearly movable along the dosing arm 2 between partly a first position, where the first duct that is connected with the container 6 is in connection with the dosing cup 2.1, partly a second position, where the container 6 is secluded from the connection with the dosing cup 2.1, which in its turn is accessible and admits to pick up bonding liquid either directly in the cup or, e.g., through a second duct 3.2 in the dosing head 3.

Instead of the dosing arm 2 being fixedly arranged on a stand, the dosing head 3 may be fixed and the dosing arm 2 linearly movable. It is of course even possible to exclude the stand 2 entirely in the two latter embodiments, which however calls for the dosing arm 2 being held in such a position that the dosing cup 2.1 is directed upwardly.

What is claimed is:

1. A dosing feeder for a bonding liquid which comprises:

a dosing arm which defines an upwardly-open dosing cup, a dosing head having a fitting and which defines a passageway in which said dosing arm can extend, and a first duct which extends through said fitting to said passageway, said fitting defining a first screw threading, and an adapter which is said positionable between said fitting and a container of bonding liquid, adaptor including a second screw threading for engagement with said first screw threading and a third screw threading for engagement with a screw threading on a container, said dosing head being movable relative to said dosing arm when located in said passageway from a first position wherein bonding liquid will flow from a container attached to said adaptor, through said first duct and to said dosing cup, to a second position wherein said dosing cup is exposed for removal of bonding liquid therefrom.

2. A dosing feeder according to claim 1, wherein said dosing head defines a second duct which, when said dosing head is in said second position, provides access to said dosing cup.

3. A dosing feeder according to claim 2, wherein said dosing arm is cylindrical, and said dosing head is rotatable therearound between said first and second positions.

4. A dosing feeder according to claim 3, wherein said passageway is cylindrical, wherein said first duct extends away from said cylindrical passageway in a first generally radial direction, and wherein said second duct extends away from said cylindrical passageway in a second generally radial direction generally opposite said first direction.

5. A dosing feeder according to claim 1, including a stand to which said dosing arm is attached.

6. A dosing feeder according to claim 1, wherein said fitting is externally threaded, and wherein said adapter defines a first side which includes a first internally threaded bore for engagement with said fitting and an opposite second side which includes a second internally threaded bore for engagement with an externally threaded neck of said container.

7. A dosing feeder according to claim 6, wherein said adapter defines a passageway which extends between said first bore and said second bore.

* * * * *